United States Patent [19]

Hosoda

[11] 4,354,749
[45] Oct. 19, 1982

[54] ENDOSCOPIC PHOTOGRAPHING APPARATUS

[75] Inventor: Seiichi Hosoda, Fuchu, Japan

[73] Assignee: Olympus Optical Co., Ltd., Tokyo, Japan

[21] Appl. No.: 294,332

[22] Filed: Aug. 19, 1981

[30] Foreign Application Priority Data

Sep. 3, 1980 [JP] Japan ................................. 55-121879

[51] Int. Cl.³ .................... G03B 29/00; A61B 1/04; G03B 15/03
[52] U.S. Cl. ........................................ 354/33; 354/62; 354/173
[58] Field of Search ................. 354/32, 33, 60 F, 62, 354/75, 76, 79, 126, 173; 350/19; 128/6-9

[56] References Cited

U.S. PATENT DOCUMENTS 3,737,721 6/1973 Ogawa .
3,769,888 11/1973 Quinn .
4,086,583 4/1978 Takahashi .
4,153,356 5/1979 Hama .

*Primary Examiner*—William B. Perkey
*Attorney, Agent, or Firm*—Frishauf, Holtz, Goodman and Woodward

[57] ABSTRACT

An endoscopic photographing apparatus has an endoscope, a camera mounted to an eyepiece section of this endoscope, and a light supply unit to which is connected a connector section of the endoscope. The camera is provided with a photosensitive element for generating a photoelectric signal corresponding to the intensity of light which enters it via an image guide of the endoscope, an exposure calculating circuit for calculating the exposure from the photoelectric signal from this photosensitive element to generate a quenching signal based upon the calculated exposure, and a buffer circuit for outputting a signal of high level in response to the quenching signal from this exposure calculating circuit. When the signal of high level from this buffer circuit is input to the exposure calculating circuit of the light supply unit, the exposure calculating circuit immediately outputs a signal for terminating the light flash of the light source.

4 Claims, 3 Drawing Figures

ENDOSCOPIC PHOTOGRAPHING APPARATUS

BACKGROUND OF THE INVENTION

The present invention relates to an endoscopic photographing apparatus, and more particularly to an endoscopic photographing apparatus with an automatic exposure function.

In conventional endoscopic photographing apparatuses, automatic exposure photography is performed by calculating the output from a photosensitive element of the endoscope by means of an automatic exposure calculating circuit in a light supply unit, and terminating the emission of light from a light source in response to an output from the automatic exposure calculating circuit. However, such an automatic exposure photographing apparatus cannot calculate the exposure accurately, because of the response delay of the photosensitive element and the noise introduced by the long transmission line through which the output from the photosensitive element passes to the endoscope, etc. This tends to lead to incorrect exposure. To solve this problem, an automatic exposure calculating circuit is preferably provided in the camera. However, this will cause inconvenience to users, since it is impossible in this case to directly combine the camera having an automatic exposure calculating circuit with the light source unit having a similar circuit.

SUMMARY OF THE INVENTION

It is an object of this invention to provide an endoscopic photographing apparatus which allows endoscopic photography under automatic exposure by easily combining a camera including a built-in automatic exposure circuit with a light source unit containing a similar built-in circuit.

According to this invention, there is provided an endoscopic photographing apparatus comprising a photosensitive element for detecting light reflected from a subject via an image guide of an endoscope, an integrator for integrating the output from this photosensitive element, a comparator for generating a quenching signal when the integrated output from this integrator reaches a predetermined value, and means for instantaneously raising the level of this quenching signal to supply this quenching signal via the endoscope to a quenching circuit in a light source unit of the endoscope.

DETAILED DESCRIPTION OF THE PREFERRED EMBODIMENTS

Figure 1:
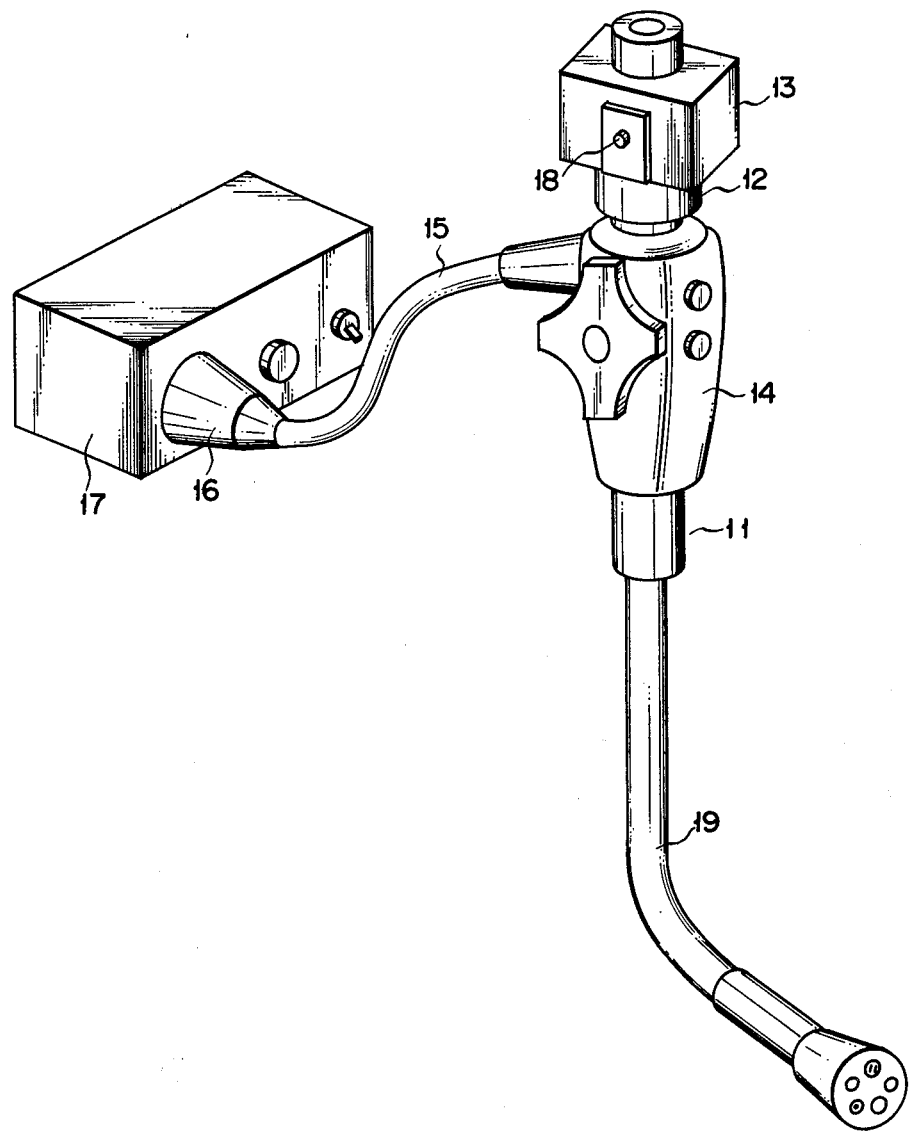
FIG. 1 is a perspective view of an endoscopic photographing apparatus according to an embodiment of this invention.

In an endoscopic photographing apparatus shown in FIG. 1, an endoscope camera 13 is mounted to an eyepiece section 12 of an endoscope 11, and a connector 16 of a universal cord 15 extending from an endoscope control section 14 is connected to a light supply unit 17. The endoscope camera 13 is provided with a release button 18.

Figure 2:
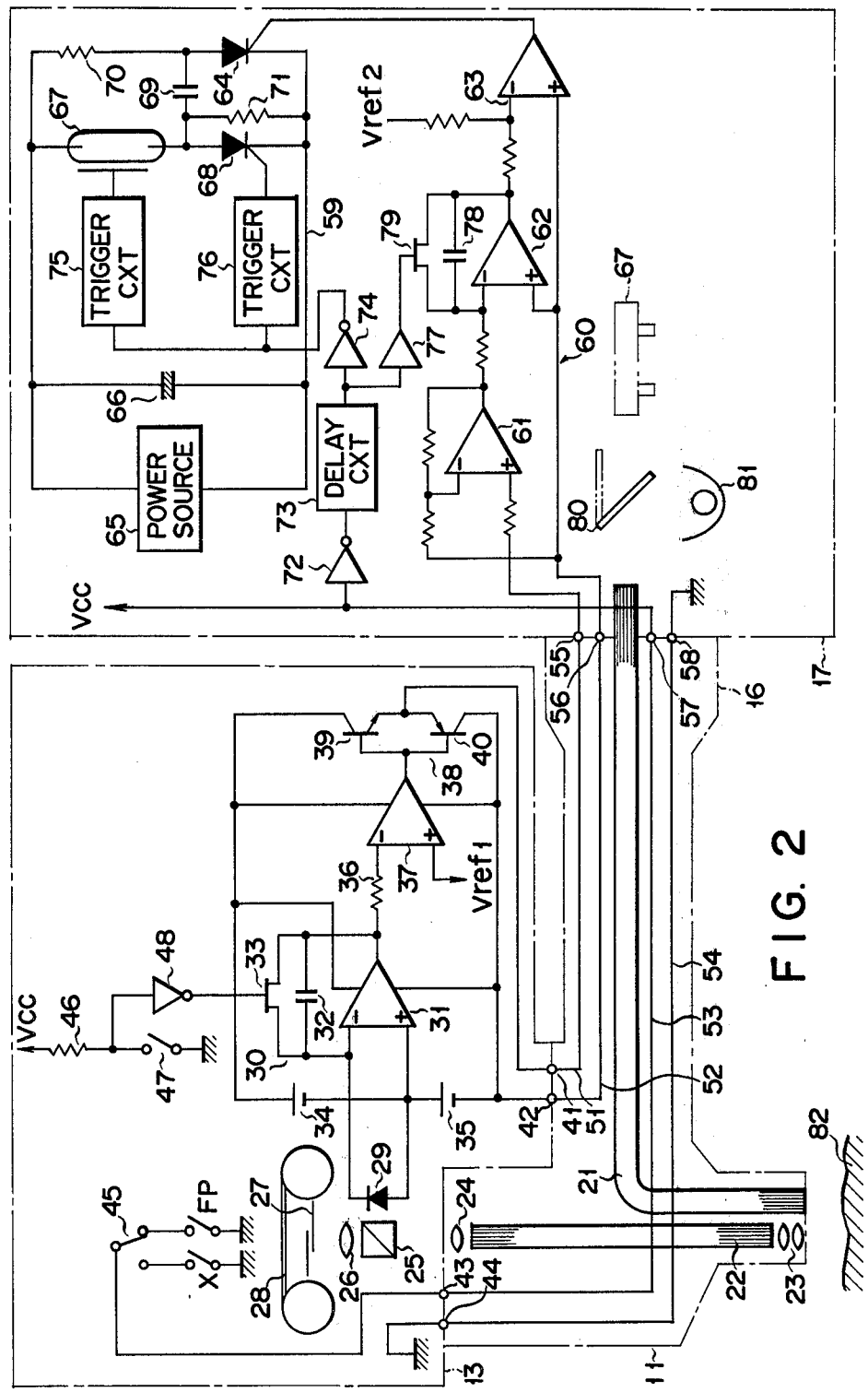
FIG. 2 is a circuit diagram of the endoscopic photographing apparatus shown in FIG. 1.

FIG. 2 shows the internal structure of the endoscopic photographing apparatus of FIG. 1. Referring to this figure, a light guide 21 and an image guide 22 are provided in the endoscope 11. The light guide 21 extends from the front end of an insertion tube 19 into the light supply unit 17, and the image guide 22 extends from an objective lens 23 to an eyepiece lens 24.

In the endoscope camera 13 are sequentially arranged a beam splitter 25, a photographic lens 26, a shutter 27 and a film 28 along the optical axis of the image guide 22 of the endoscope 11. A photosensitive element (e.g. photodiode) 29 is disposed on the side of the beam splitter 25, and is connected between the inverting and non-inverting input terminals of an operational amplifier 31 of an integrating circuit 30. The non-inverting input terminal of this operational amplifier 31 is connected to a node of power sources 34 and 35, and an integrating capacitor 32 and an analog switch, for example, a MOSFET 33, are connected in parallel between the inverting input terminal and the output terminal of the amplifier 31. The output terminal of the integrating circuit 30 is connected via a resistor 36 to the inverting input terminal of an operational amplifier 37 functioning as a comparator. A reference voltage Vref1 is applied to the non-inverting input terminal of this operational amplifier 37. The output terminal of the operational amplifier 37 is connected to the bases of an npn transistor 39 and a pnp transistor 30 which constitute a buffer circuit 38. The npn transistor 39 has its collector connected to the anode of the power source 34 and its emitter, via the eitter-collector path of the pnp transistor 40, to the cathode of the power supply 35. The output terminal of the buffer circuit 38 and the cathode of the power source 35 are respectively connected to connecting terminals 41 and 42. Connecting terminals 43 and 44 are respectively connected to the common contact of a changeover switch 45, and ground. The two contacts of the changeover switch 45 are grounded respectively through synchronous contact swiches X and FP. A power source Vcc is grounded via a resistor 46 and a switch 47, and the node of the resistor 46 and the switch 47 is connected to the gate of the MOSFET 33 via an inverter 48.

The connecting terminals 43 and 44 are connected to connecting terminals 55 to 58 of the connector 16 through signal lines 51 to 54, respectively, in the endoscope 11.

In the light supply unit 17, the connecting terminal 55 is connected to an amplifier circuit 61 of an automatic exposure calculating circuit 60, and this amplifier circuit 61 has its output terminal connected to an integrating circuit 62. The output terminal of the integrating circuit 62 is connected to a comparator circuit 63. The output terminal of the comparator circuit 63 is connected to the gate of a quenching thyristor 64 of a light flash control circuit 59. In this light flash control circuit 59, a parallel circuuit formed of a main capacitor 66 and a series circuit of a strobe tube (flash tube) 67 and a main thyristor 68 are connected in parallel with a power source 65. To the main thyristor 68 is connected in parallel a series circuit formed of a quenching capacitor 69 and the quenching thyristor 64. The quenching capacitor 69 is charged through a charge line formed of a resistor 70, the quenching capacitor 69, and a resistor 71.

The connecting terminal 57 is connected to the power source Vcc as well as to a delay circuit 73 via an inverter 72. The output terminal of the delay circuit 73 is connected to the input terminals of trigger circuits 75 and 76 via an inverter 74. The output terminal of the delay circuit 73 is also connected, via a buffer circuit 77, to an analog switch, for example, the gate of a MOSFET 79, connected in parallel with an integrating capacitor 78 of the integrating circuit 62. The output terminals of the trigger circuits 75 and 76 are respectively connected to the trigger electrode of the strobe tube 67 and to the gate of the main thyristor 68. The strobe tube 67 is disposed opposite to the light guide 21 through a light path changeover mirror 80, as shown by the dot and dash line. When the mirror 80 is in the position indicated by the solid line, light from a halogen lamp 81 is guided to the light guide 21 by the mirror 80.

In the endoscopic photographing apparatus described above, when the contact switch FP is selected by the changeover switch 45 of the camera 13 and the release button 18 of the camera 13 is depressed, the contact switch FP is closed before the shutter 27 is opened, and a synchronizing signal is transmitted through the endoscope signal line 53 and the inverter 72 of the light supply unit 17 to the delay circuit 73. The delay circuit 73 generates an output after a predetermined delay time, and this delayed output energizes the trigger circuits 75 and 76 via the invertor 74, and also turns off the MOSFET 79 via the buffer 77. The outputs of the trigger circuits 75 and 76 trigger the strobe tube 67 and the main thyristor 68 to cause the strobe tube 67 to flash. During this time period, the switch 47 is closed in synchronism with the opening of the shutter 27 in the camera 13, whereby the MOSFET 33 of the integrating circuit 30 is turned off to start the integrating operation. The light emitted by the strobe tube 67 illuminates a subject 82 by way of the light guide 21 of the endoscope 11. The light reflected from the subject 82 exposes the film 28 via the objective lens 23, the image guide 22, the eyepiece lens 24, the beam splitter 25, the lens 26 and the open shutter 27 of the camera 13. And at this point, the photosensitive element 29 converts the part of the light reflected by the beam splitter 25 into an electrical signal. The output of the photosensitive element 29 is integrated by the integrating circuit 30. The integrated output is compared with the reference voltage Vref1 by the comparator 37. When the integrated output reaches the reference voltage Vref1, the output from the comparator 37 turns on the transistor 39 and turns off the transistor 40. Therefore, the sum of the voltages from the B power sources 34 and 35 is applied to the amplifier circuit 61 of the light source unit 17 to instantly saturate the integrating circuit 62. In other words, the output from the integrating circuit 62 reaches the reference voltage Vref2 of the comparator circuit 63 in an instant, and thus the output from the comparator circuit 63 turns on the quenching thyristor 64 of the light flash control circuit 59. The main thyristor 68 is reversely biased by the charge voltage of the quenching capacitor 69 to be turned off, which terminates the flash radiation of the strobe tube 67.

As described above, since the output from the automatic exposure calculating circuit of the camera causes the output of the integrating circuit of the automatic exposure calculating circuit in the light source unit to be instantly increased to the reference voltage, the camera with the automatic exposure calculating circuit may be applied to a light supply unit with or without an automatic exposure calculating circuit, whereby interchangeability between light supply units of both types is achieved.

It is to be understood that since the reference voltage applied to the comparator of the automatic exposure calculating circuit in the light supply unit is set by an exposure constant such as the ASA, and the output of the integrating circuit is increased to the reference voltage in an instant by the quenching signal from the camera, the integrated output will readily reach the reference voltage even if the latter is set near the power source voltage.

Although the integrator is saturated in the embodiment described above, the same effects will be obtainable when the reference voltage of the comparator has been set low, even with the integrator being unsaturated, because the light emission from the light source can be terminated if the integrated output reaches the reference voltage.

During the time interval which the output of the integrator reaches the reference voltage, the film is exposed. However, this time is too short to affect the exposure even with the time constant of the integrator, since the output voltage level from the automatic exposure calculating circuit is very high.

Figure 3:
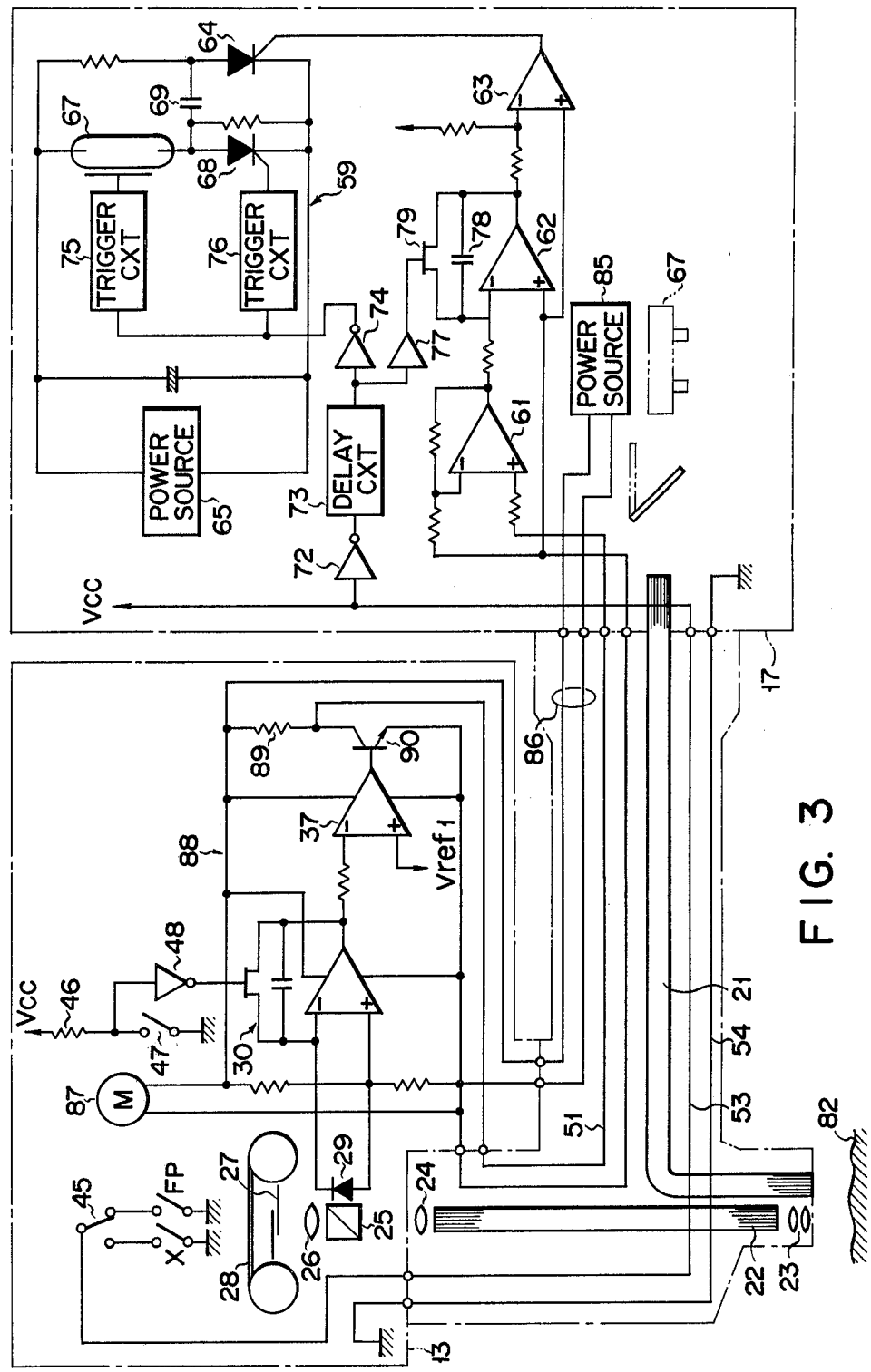
FIG. 3 is a circuit diagram of an endoscopic photographing apparatus according to another embodiment of this invention.

Although B power sources have been provided in the embodiment shown in FIG. 2, the output voltage from a motor power source 85 provided in the light supply unit 17 may be utilized, as shown in FIG. 3. The motor power source 85 is connected via a power source line 86 of the endoscope 11 to, for example, a film winding motor 87, as well as to an automatic exposure calculating circuit 88 of the camera 13. In this case, a series circuit formed of a resistor 89 and a transistor 90 is connected to the motor power source 85 via the power supply line 86 in the automatic exposure circuit 88, and the output terminal of the comparator 37 is connected to the base of the transistor 90. According to this embodiment, when the integrated output from the integrating circuit 30 reaches the reference voltage Vref1 of the comparator 37, the output from the comparator 37 turns off the transistor 90 to apply a motor voltage of high level to the amplifier circuit 61 of the automatic exposure calculating circuit 60 of the light supply unit 17 through the signal line 51 of the endoscope 11. Thus, the integrating circuit 62 is instantly saturated and the light emission control circuit 59 terminates the flash radiation of the strobe tube 67.

The same effects can be obtained with the embodiment shown in FIG. 3 as that in FIG. 2, but the power sources need not be provided within the camera. In the embodiment shown in FIG. 3, the same parts as those of the embodiment illustrated in FIG. 2 are designated with the same reference numerals, and the description thereof is omitted.

In FIGS. 2 and 3, the automatic exposure calculating circuit is provided in the camera. However, if the camera is not provided with an automatic exposure calculating circuit, the photoelectric signal from the photosensitive element provided in the camera or the endoscope may be input to the exposure calculating circuit of the light supply unit for calculating the exposure.

What is claimed is:

1. An endoscopic photographing apparatus having an endoscope with an eyepiece section, a connector section, a light guide and an image guide, an endoscope camera detachably mounted to the eyepiece section of the endoscope, and a light supply device to which the connector section of the endoscope is detachably coupled, in which said camera comprises a photosensitive element for generating a photoelectric signal corresponding to the intensity of light which enters the camera via said image guide, an exposure calculating circuit for calculating the exposure based on said photoelectric signal from said photosensitive element to output a quenching signal at a predetermined exposure, and high level signal output means for outputting a signal of high level in response to said quenching signal from said exposure calculating circuit to guide this quenching signal to said light source device through a signal line provided in said endoscope.

2. An endoscopic photographing apparatus according to claim 1, wherein said light supply device has a light emission control circuit having a light source and means for initiating and terminating the light emission of said light source, and an exposure calculating circuit for inputting to said light emission control circuit a signal for terminating the light emission, said exposure calculating circuit being responsive to said signal of high level from the high level signal outputting means of said camera to immediately input to said light emission control circuit said signal for terminating the light flash.

3. An endoscopic photographing apparatus according to claim 1 or 2, wherein said light source device has a power source circuit, and said camera has a film winding motor, said power source circuit supplying power to said film winding motor and said exposure calculating circuit of said camera through a power source line provided in said endoscope.

4. An endoscopic photographing apparatus according to claim 1 or 2, wherein said exposure calculating circuit of said camera comprises an integrating circuit for integrating said photoelectric signal from said photosensitive element to output an integrated output, and a comparator for comparing said integrated signal from said integrating circuit with a reference signal to generate a quenching signal; and said high level signal output means comprises circuit means which is connected to a power source of high level and responsive to said quenching signal from said comparator to apply a voltage of high level from said high level power source to said light supply device.

* * * * *